(12) United States Patent
Kawahara

(10) Patent No.: US 8,453,347 B2
(45) Date of Patent: Jun. 4, 2013

(54) FOOTWEAR SOLE INSERT AND FOOTWEAR

(75) Inventor: Takemasa Kawahara, Osaka (JP)

(73) Assignee: Sea Shell Co., Ltd., Osaka (JP)

( * ) Notice: Subject to any disclaimer, the term of this patent is extended or adjusted under 35 U.S.C. 154(b) by 686 days.

(21) Appl. No.: 12/452,205

(22) PCT Filed: Jul. 10, 2008

(86) PCT No.: PCT/JP2008/062444
§ 371 (c)(1),
(2), (4) Date: Feb. 5, 2010

(87) PCT Pub. No.: WO2009/008462
PCT Pub. Date: Jan. 15, 2009

(65) Prior Publication Data
US 2010/0132222 A1    Jun. 3, 2010

(30) Foreign Application Priority Data
Jul. 10, 2007 (JP) .................. 2007-180962

(51) Int. Cl.
*A43B 7/141* (2006.01)
*A43B 7/1445* (2006.01)
*A43B 7/22* (2006.01)

(52) U.S. Cl.
USPC ..................... 36/44; 36/154; 36/88

(58) Field of Classification Search
USPC ............... 36/91, 94, 155, 169, 172, 174, 145, 36/43, 71, 44, 154
See application file for complete search history.

(56) References Cited

U.S. PATENT DOCUMENTS

| | | | |
|---|---|---|---|
| 2,081,474 A * | 5/1937 | Burns | 36/174 |
| 2,760,281 A * | 8/1956 | Cosin | 36/154 |
| 2,785,480 A * | 3/1957 | MacCarone | 36/91 |
| 3,861,398 A * | 1/1975 | Leydecker | 36/174 |
| 4,020,570 A * | 5/1977 | Shames | 36/44 |
| 4,408,402 A * | 10/1983 | Looney | 36/43 |
| 4,689,898 A * | 9/1987 | Fahey | 36/43 |
| 4,866,860 A * | 9/1989 | Blissett et al. | 36/28 |
| 4,955,148 A * | 9/1990 | Padilla | 36/44 |

FOREIGN PATENT DOCUMENTS

| | | |
|---|---|---|
| JP | 9-224703 | 9/1997 |
| JP | 2000-354503 | 12/2000 |
| JP | 2002-282011 | 10/2002 |

* cited by examiner

*Primary Examiner* — Jila M Mohandesi
(74) *Attorney, Agent, or Firm* — Jordan and Hamburg LLP

(57) ABSTRACT

To provide a footwear sole insert and footwear that would allow performing the fundamental motion of grasping through regulation and promotion of the formation of a functional fundamental arch line linking the cuneocuboid joint areas at cuboidal bone edges of the foot parts with the second and third MP joint areas thereof to thereby making it possible to basically solve alignment abnormality and functional failure. A sole insert is provided with a raised ridge face brought into contact with the region of the foot part extending from the vicinity of the cuneocuboid joint area at edges of cuboids to the vicinity of the proximal phalanxes at the MP joint area between second metatarsals and third metatarsals so as to elevate the region and hold the same in archlike form.

2 Claims, 5 Drawing Sheets

(a)

(b)

(a)

(b)

FOOTWEAR SOLE INSERT AND FOOTWEAR

FIELD OF THE INVENTION

The present invention relates to a footwear sole insert and footwear that can regulate and reinforce the function of the arch structure of the foot region, and can demonstrate an effect in prevention and treatment of flat foot, hallux valgus, and other lower extremity ailments.

BACKGROUND OF THE INVENTION

During standing or walking, a repeated load is continuously applied in excess to the foot region due to deformations and the like of the skeletal structure. When this occurs, so-called hallux valgus, flat foot, and other alignment abnormalities and lower extremity ailments are brought about, and if the symptoms worsen, then walking itself becomes difficult and other important problems occur that make a person unable to sustain daily life. The skeletal structure and form of the foot have therefore been analyzed, and a variety of sole inserts and footwear have been proposed with the purpose of preventing and treating functional failures of the foot region.

For example, footwear has been proposed in which the emphasis is on the direction of movement of the load on the foot region during walking and which can be used in the treatment and prevention of lower extremity ailments according to an original theory (see Patent Document 1). Shoes and shoe sole inserts have also been proposed in which the arch structure of the foot region can be regulated and the function of the foot can be reinforced (see Patent Document 2). A variety of other footwear and sole inserts have been proposed according to analyses of the skeletal structure of the foot.

Patent Document 1: JP-A 2005-347
Patent Document 2: JP-A 9-224703

It is, however, impossible to find a radical solution unless a solution strategy is adopted based on the fundamental concept and function of the foot region, despite the fact that a variety of resolution means have been proposed with the purpose of preventing and treating hallux valgus and other alignment abnormalities and functional failures of the foot region in the footwear and sole inserts proposed in the past.

As shown in FIGS. 6(a) and 6(b), the foot region of a human being is constructed from many bones, functions in an intricate manner, and is formed into an arch structure so that force resulting from adaptation to uneven terrain and from body weight and body movement is transmitted to the surface. It is generally assumed that the arch structure comprises an internal longitudinal arch (an arc in which the navicular is at the peak, the rear starts from the point of contact with the calcaneus, and the front is made from the first metatarsal), an external longitudinal arch (an arc in which the cuboid is at the peak, the rear starts from the point of contact with the calcaneus, and the front is made from the fifth metatarsal), and a lateral arch (an arc made from the metatarsals), as shown in the drawings. The main role of the foot region is believed to be to distribute loads and absorb shock to the sole, hoist up the arch using a windlass structure, and move body weight using lever action.

However, past methods of thinking about the arch structure and knowledge of the role of the structure have been based on observations of one portion of the foot region, and cannot be regarded to take into account the fundamental functionality of the foot region. In other words, in anthropoids other than humans, the configurations of the hands and feet are similar, and the feet can perform the motion of grasping an object in the same manner as the hands. Even though human feet originally had a catching function for grasping objects in the same manner as the hands, humans started bipedal walking, the structure of the foot evolved to suit bipedal walking, and a decline in the catching function was caused by the birth of footwear. Therefore, in order to comprehend the fundamental functionality of the foot, observation should be returned to the original structure of the foot that could grasp objects.

When the human foot region is considered from an anatomical point of view, a structure exists that is capable of a grasping motion using the closing motion of the thumb and four toes, and the bending motion from the MP joints. When looking at the wrinkles of the sole, the biggest wrinkle exists in the long axial direction to the side of the ball of the thumb, and this wrinkle exists in a portion that, functionally, can perform bending in the same manner as seen in the hand. For this reason as well, the fundamental function of the human foot is in the grasping motion, and the above-mentioned past concept of the arch of the foot should also be considered based on the fundamental concept of the function of the foot region itself. The line that links the cuboidal bone edges and the cuneocuboid joint areas with the second and third MP joint areas, which form the basis of the grasping motion, should be thought of as the functional fundamental arch. This is because the fundamental arch forms a peak, the above-mentioned internal and external longitudinal arches are disposed to the left and right of the fundamental arch, and these arches would not be established without this peak.

Measures designed to solve the problems of hallux valgus, flat foot, and other alignment abnormalities and functional disorders of the foot region differ widely depending on whether the foundation of the foot region is perceived as a structure for grasping or whether it is perceived simply as a structure that collapses like a spring. To find a radical solution to the problems of the foot region, it is first necessary to promote the original function and motion of grasping in the foot region, whereas the products proposed in the past were not configured based on such a fundamental function and motion.

The present invention was therefore perfected in view of the fact that a radical solution can be expected to be found for alignment abnormalities and functional failures by being able to perform the heretofore ignored above-mentioned fundamental motion based on the form of the functional fundamental arch line that links the cuboidal bone edges and the cuneocuboid joint areas with the second and third MP joint areas of the foot region, and an object of the present invention is to provide a footwear sole insert and footwear that can regulate and promote the form of this arch.

SUMMARY OF THE INVENTION

In order to resolve the above-mentioned problem, the present invention was configured as follows. The footwear sole insert of the present invention is characterized in that a raised ridge face is formed and brought into contact with a region extending from the vicinity of a cuneocuboid joint area at the edge of the cuboid to the vicinity of the proximal phalanxes at an MP joint area between the second metatarsal and third metatarsal so as to elevate the region and hold the same in archlike form, and a depression is formed to accommodate the MP joints in the MP joint area.

The footwear of the present invention is characterized in having a footwear inner bottom surface comprising a raised ridge face formed and brought into contact with a region extending from the vicinity of a cuneocuboid joint area at the edge of the cuboid to the vicinity of the proximal phalanxes at an MP joint area between the second metatarsal and third metatarsal so as to elevate the region and hold the same in archlike form, and further comprising a depression formed to accommodate the MP joints in the MP joint area.

According to the present invention, a grasping motion can be performed by the formation of a functional fundamental arch line that links the cuboidal bone edges and the cuneocuboid joint areas with the second and third MP joint areas of the foot region; mechanical stress can be reduced in loaded joints when the body weight is moved or the like during walking, and functionality can be improved when running or standing; and a radical solution can be found for the heretofore problematic hallux valgus, flat foot, and other alignment abnormalities and functional failures of the foot region.

Figure 1:
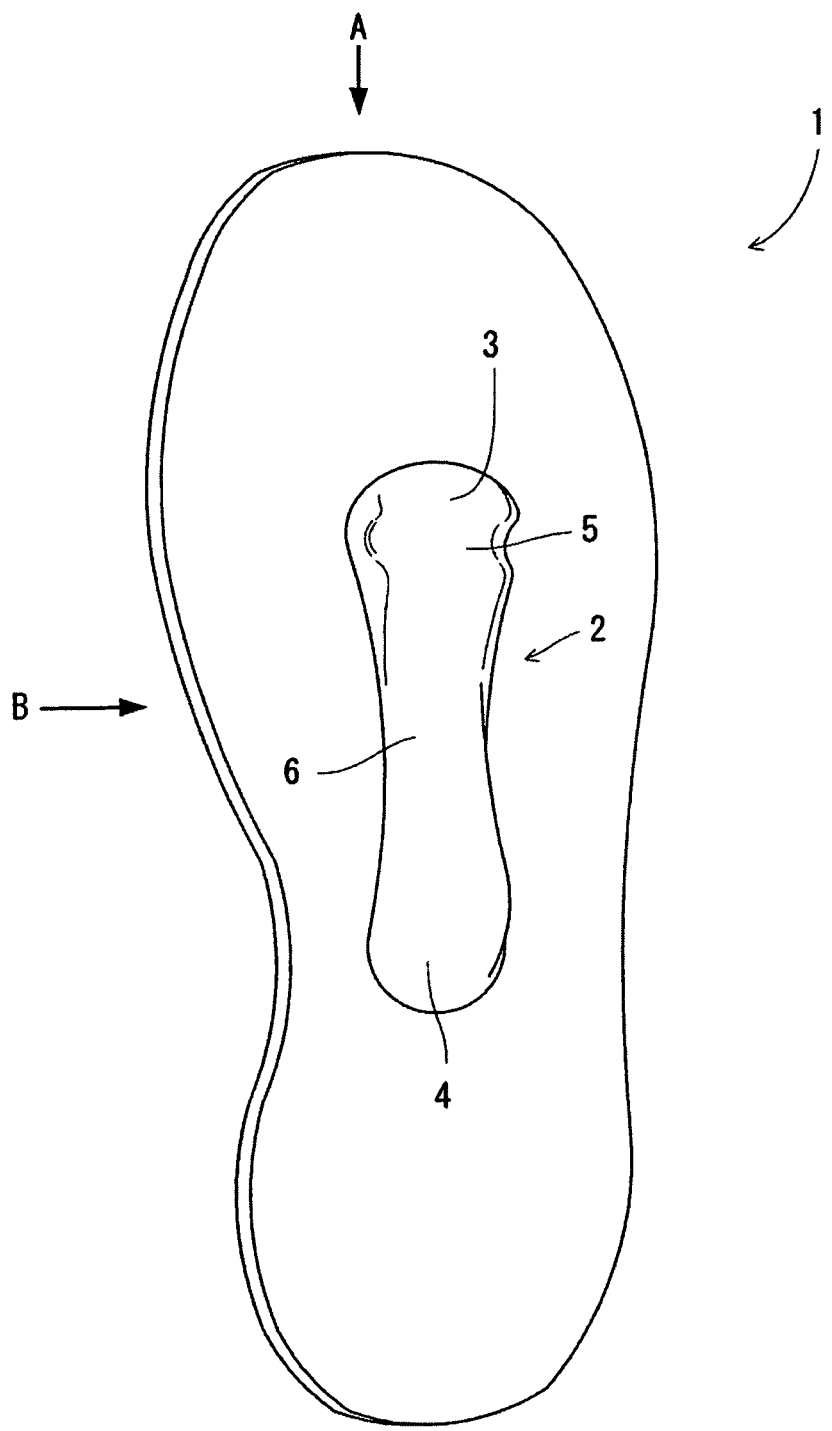
FIG. 1 is an external view showing the structure of a sole insert according to an embodiment of the present invention.

REFERENCE NUMERALS 1 sole insert
2 raised ridge surface
3 contact surface at proximal phalanx
4 contact surface at cuneocuboid joint area
5 depression
6 mountain-shaped inclined surface
10 cuboid
11 cuneocuboid joint area
12 second metatarsal
13 third metatarsal
14 MP joint area
15 proximal phalanx

DESCRIPTION OF THE PREFERRED EMBODIMENTS

An embodiment for implementing the present invention will be described in detail based on the drawings. FIG. 1 is a plan view showing the structure of a sole insert 1 according to the present invention, and FIGS. 2(a) and 2(b) are a front view and a side view of the same. The sole insert 1 is constructed from a sheet member made of a resin material having thermoplastic properties, and has a raised ridge face 2 formed in the center region as shown in the drawing. When the sole insert 1 is fitted into footwear, the raised ridge face 2 is brought into contact with the region of the foot part extending from the vicinity of the cuneocuboid joint area 11 at the edges of the cuboid 10 to the vicinity of the proximal phalanxes 15 at the MP joint area 14 between the second metatarsal 12 and the third metatarsal 13 so as to elevate the region and hold the same in archlike form as shown in FIG. 3, which displays the state of the foot region when the sole insert 1 is put in place.

The region from the vicinity of the cuneocuboid joint area 11 at the edge of the cuboid 10 to the vicinity of the proximal phalanxes 15 at the MP joint area 14 between the second metatarsal 12 and the third metatarsal 13 differs from an arch structure that is perceived as a structure that collapses like a spring in the internal longitudinal arch, the external longitudinal arch, and the lateral arch known in the past to form the foot region. This region is a location that is known as a region for forming an arch perceived as the original fundamental structure of the foot that can perform a grasping motion using the bending from the MP joints.

Figure 2:
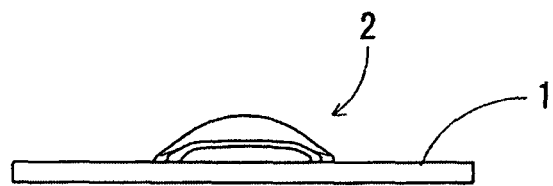
FIG. 2 is a front view and side view showing the structure of the sole insert according to an embodiment of the present invention.
Figure 2:
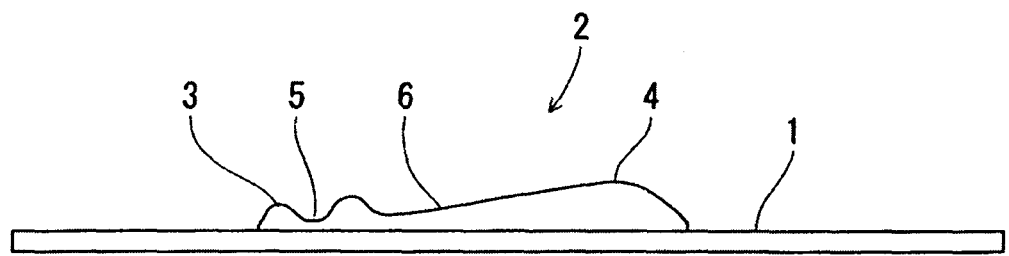
Figure 3:
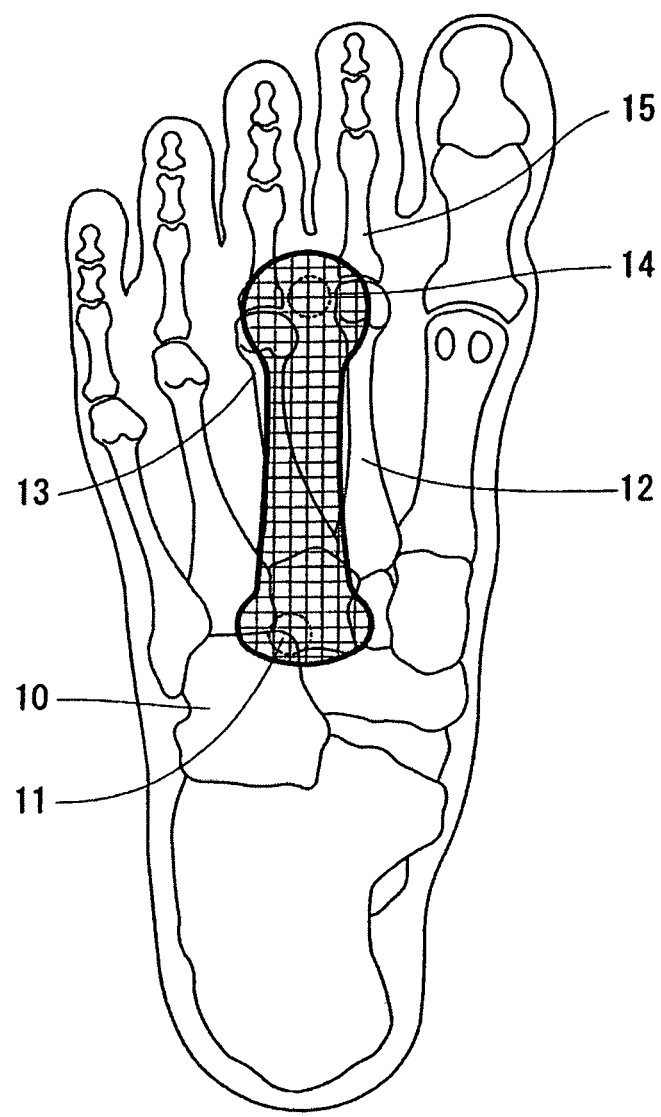
FIG. 3 is a view showing the areas with which the foot region comes into contact when placed on the sole insert.

As shown in FIG. 2, the raised ridge face 2 is formed so that a contact surface 3 at the proximal phalanxes 15 and a contact surface 4 at the cuneocuboid joint area 11 serve as respective ends, that the contact surface 3 has a depression 5 formed so that protrusions at the ends thereof accommodate the MP joint area 14, and that a sloping inclined surface 6 extends from the depression 5 to the contact surface 4 at the cuneocuboid joint area 11 in the rear. The inclined surface 6 is formed so as to rise up into a cross-sectional mountain shape, as shown in the same FIG. 2(a), and is constructed in a form that shapes the arch at the above-mentioned region when the foot is placed on the sole insert 1.

Figure 4:
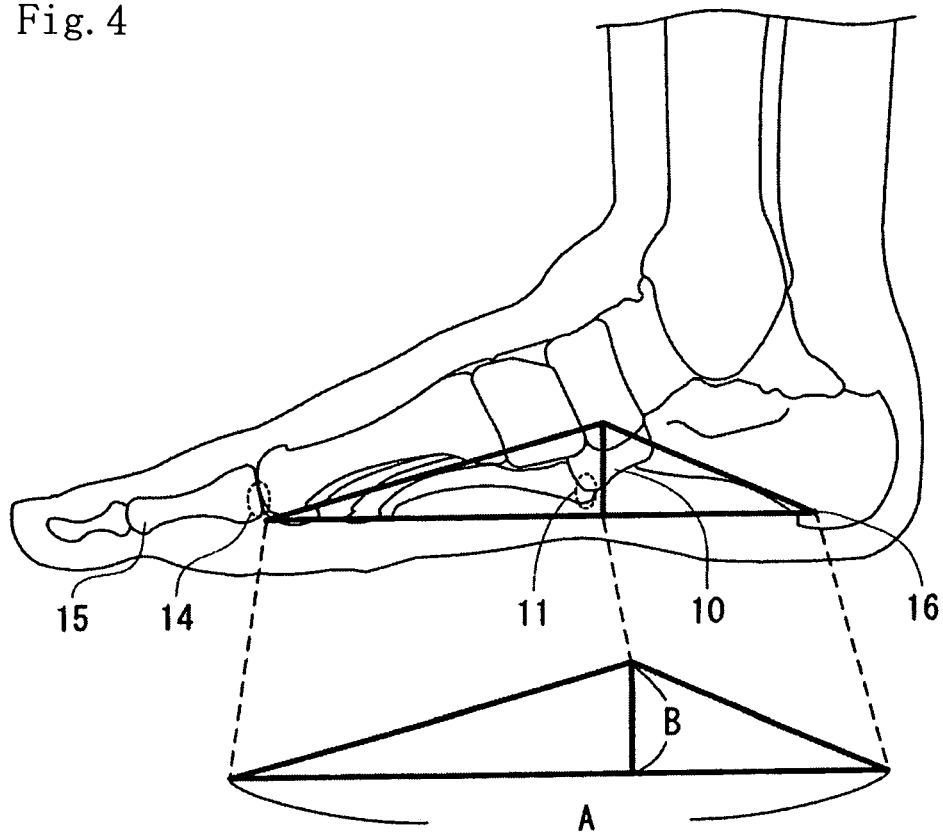
FIG. 4 is a view depicting the ratio settings in the configuration of the raised ridge surface.

The raised ridge surface 2 is formed in order to regulate such an arch, and the ratio of the fundamental form and the size of the surface is determined based on the standard method shown in FIG. 4 when an average plain scale calculation is performed in accordance with the functional anatomy of the foot region, and the result is converted into a ratio (without taking into account muscle volume).

In FIG. 4, A is the length from the vicinity of the proximal phalanxes 15 at the MP joint area 14 between the second metatarsal 12 and the third metatarsal 13, which is the distal end of the raised ridge surface 2, to the tuberosity of calcaneus 16; and B is the raised ridge height as viewed vertically from the vicinity of the cuneocuboid joint area 11 at the edge of the cuboid 10, which is the rear end of the raised ridge surface 2. Although there are differences in the alignment of high arch, flat foot, and the like due to individual feet, the ratio of A:B=3 to 30:1 is valid, as can be seen based on extensive data gathering, and the raised ridge face 2 can be formed to fit respective feet using this ratio. For example, in the case of a foot size of 23 cm, A is approximately 15 cm, and B is approximately 2.5 cm, which corresponds to a ratio of 15:2.5=6:1 and can be standardized as a general average value. The height B is 2.5 cm or less if muscle volume is taken into account.

Placing a sole insert 1 provided with such a raised ridge face 2 on the sole of footwear makes it possible to regulate and reinforce the arch of the sole of the foot, which also served as the foundation of the arch concept in the past, and to promote the recovery of the fundamental arch structure. Therefore, mechanical stress can be reduced in loaded joints when the body weight is moved or the like during walking, functionality can be improved during running or standing, and a radical solution can be found for the heretofore problematic hallux valgus, flat foot, and other alignment abnormalities and functional failures of the foot region.

In the example described above, the raised ridge face 2 on the sole insert 1 is an integrally formed structure, but the raised ridge face alone can be formed with silicone, urethane, rubber, natural resin, styrene foam, sponge, or another material having elastic properties, and can be constructed so as to be attached to an existing sole insert.

Figure 5:
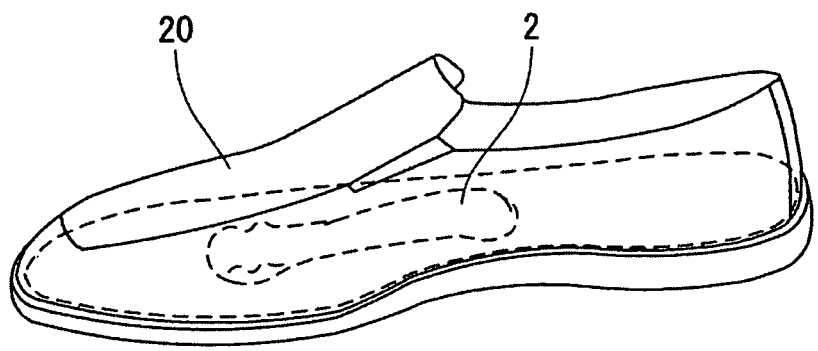
FIG. 5 is a view showing the structure of an example formed as footwear.
Figure 6:
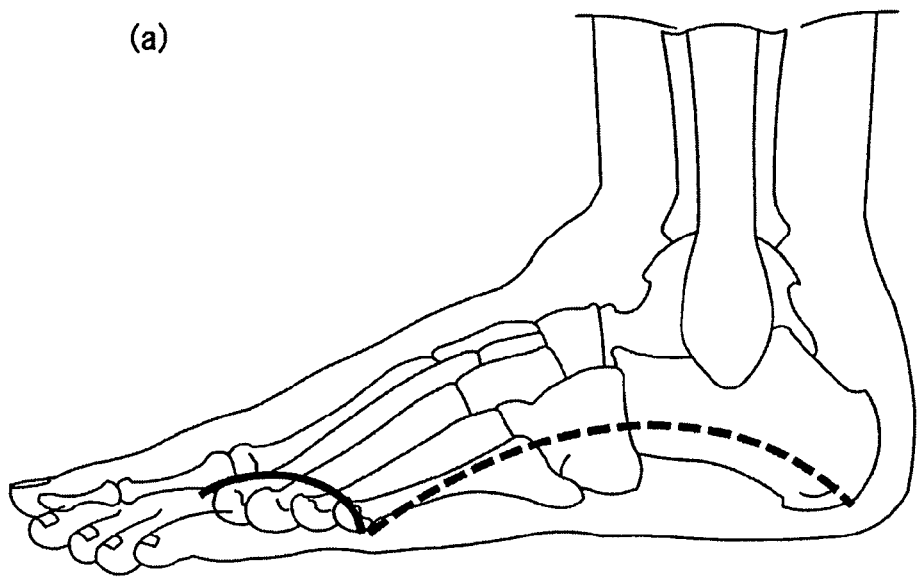
FIG. 6 is a view depicting a conventional arch structure of the foot region.
Figure 6:
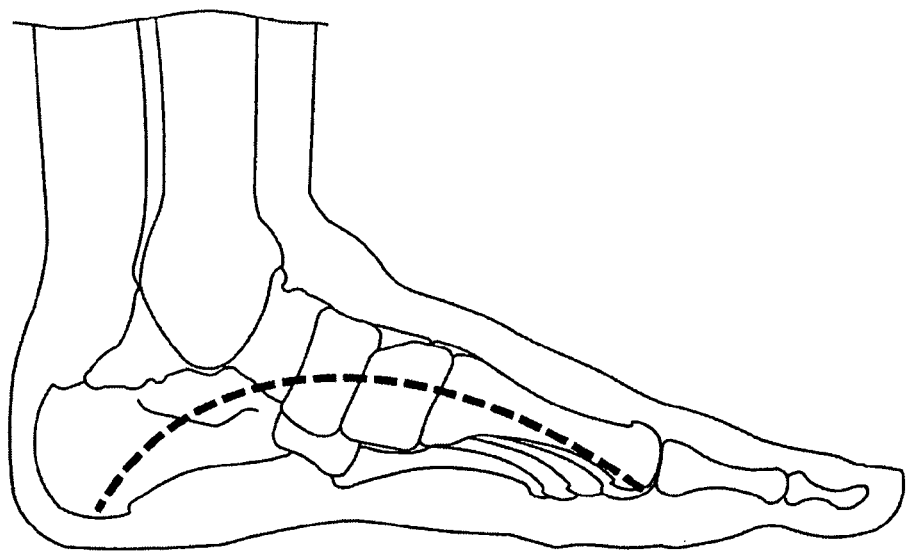

The embodiment described above is described as a footwear sole insert, but the raised ridge face 2 constructed as described above can also be formed on the inner bottom surface of footwear 20, as shown in FIG. 5. By forming the same raised ridge face 2 as described above in the footwear itself, abnormalities of the fundamental arch structure of the foot region can be regulated, functional recovery of the arch can be accomplished, and the exact same effect can be displayed.

The present invention is configured so as to be applicable as a sole insert in existing footwear in general, can be applied as the sole portion of footwear in general, and can also be used in slippers, sandals, and the like. The invention can further be used as the structure for the sole portion of socks, stockings, supporters, and the like, and can be used even in clothing that is in contact with the sole of the foot in order to regulate the most fundamental arch structure in the foot region.

The invention claimed is:

1. A footwear sole insert comprising:
   a sheet member configured to extend a length of a wearer's foot and having a uniform thickness, the sheet member having a first face adapted for receiving contact with the wearer's foot, the sheet member having a distal end toward the wearer's toes and a proximal end toward the wearer's heel;
   a raised ridge face formed at the sheet member first face, the insert having a thickness along all of said raised ridge exceeding said uniform thickness and the raised ridge face configured to be brought into contact with a region of the wearer's foot extending from a vicinity of a cuneocuboid joint area at a proximal edge of a cuboid to a vicinity of proximal phalanxes at an MP joint area between a second metatarsal and a third metatarsal so as to elevate the region and hold the same in archlike form, the raised ridge face extending in a lengthwise direction from a first end away from the distal end of the sheet member to second end away from he proximal end of the sheet member, the raised ridge face extending in a widthwise direction from a first side away from a first side edge of the sheet member to a second side away from a second side edge of the sheet member;
   a depression formed within the raised ridge face toward a distal end of the raised ridge face to accommodate MP joints in the MP joint area; and
   a sloping inclined surface formed along the raised ridge face proximal to the depression, the insert having a greatest thickness at a proximal end of the sloping inclined surface.

2. Footwear having a footwear inner bottom surface insole comprising:
   a sheet member configured to extend a length of a wearer's foot and having a uniform thickness, the sheet member having a first face adapted for receiving contact with the wearer's foot, the sheet member having a distal end toward the wearer's toes and a proximal end toward the wearer's heel;
   a raised ridge face formed at the sheet member first face, the insole having a thickness along all of said raised ridge exceeding said uniform thickness and the raised ridge face configured to be brought into contact with a region of the wearer's foot extending from a vicinity of a cuneocuboid joint area at a proximal edge of a cuboid to a vicinity of proximal phalanxes at an MP joint area between a second metatarsal and a third metatarsal so as to elevate the region and hold the same in archlike form, the raised ridge face extending in a lengthwise direction from a first end away from the distal end of the sheet member to second end away from he proximal end of the sheet member, the raised ridge face extending in a widthwise direction from a first side away from a first side edge of the sheet member to a second side away from a second side edge of the sheet member;
   a depression formed within the raised ridge face toward a distal end of the raised ridge face to accommodate MP joints in the MP joint area; and
   a sloping inclined surface formed along the raised ridge face proximal to the depression, the insole having a greatest thickness at a proximal end of the sloping inclined surface.

\* \* \* \* \*